(12) United States Patent
Nelson (10) Patent No.: US 7,387,624 B2
(45) Date of Patent: Jun. 17, 2008

(54) SQUEEZE-ACTUATED CATHETER CONNECTER AND METHOD

(75) Inventor: Brian D. Nelson, Birchwood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/355,627

(22) Filed: Feb. 16, 2006

(65) Prior Publication Data

US 2006/0264911 A1 Nov. 23, 2006

Related U.S. Application Data

(60) Provisional application No. 60/682,949, filed on May 20, 2005.

(51) Int. Cl.
*A61M 25/16* (2006.01)
*A61M 25/18* (2006.01)
*A61M 39/00* (2006.01)
*A61M 39/10* (2006.01)

(52) U.S. Cl. ........................ 604/536; 604/533
(58) Field of Classification Search ........ 604/533–539, 604/508, 513, 167.06, 240, 243
See application file for complete search history.

(56) References Cited

U.S. PATENT DOCUMENTS

| | | | |
|---|---|---|---|
| 2,815,227 A | 12/1957 | Cullen et al. | |
| 3,447,819 A | 6/1969 | Borsum et al. | |
| 3,659,881 A | 5/1972 | Tinsley et al. | |
| 3,731,955 A | 5/1973 | Borsum et al. | |
| 3,983,203 A | 9/1976 | Corbett | |
| 4,013,310 A | 3/1977 | Dye | |
| 4,193,616 A | 3/1980 | Sarson et al. | |
| 4,310,001 A | 1/1982 | Comben | |
| 4,323,065 A | 4/1982 | Kling | |
| 4,334,551 A | 6/1982 | Pfister | |
| 4,405,163 A | 9/1983 | Voges et al. | |
| 4,526,572 A | 7/1985 | Donnan et al. | |
| 4,581,012 A | 4/1986 | Brown et al. | |
| 4,592,749 A | 6/1986 | Ebling et al. | |

(Continued)

FOREIGN PATENT DOCUMENTS

AU    A-21021/83    5/1985

(Continued)

OTHER PUBLICATIONS

U.S. Appl. No. 11/057,666, filed Feb. 14, 2005, Cross.
U.S. Appl. No. 11/393,089, filed Mar. 30, 2006, Sage.

*Primary Examiner*—Kevin C. Sirmons
*Assistant Examiner*—Andrew M Gilbert
(74) *Attorney, Agent, or Firm*—Mueting, Raasch & Gebhardt, P.A.

(57) ABSTRACT

A connector for coupling medical tubing (e.g., a catheter) to an implantable medical device. The connector, in one embodiment, may include a retaining member surrounding an optional housing. The retaining member may have at least one locking finger that extends through at least one corresponding window in the housing and selectively engages a stem of the medical device to retain the end of the catheter relative thereto. Application of a compressive force applied to the retaining member may cause the locking finger(s) to withdraw from the stem and release the catheter.

5 Claims, 7 Drawing Sheets

U.S. PATENT DOCUMENTS

| | | | |
|---|---|---|---|
| 4,610,468 A | 9/1986 | Wood | |
| 4,632,435 A | 12/1986 | Polyak | |
| 4,636,204 A | 1/1987 | Christopherson et al. | |
| 4,647,082 A | 3/1987 | Fournier et al. | |
| 4,650,473 A | 3/1987 | Bartholomew et al. | |
| 4,652,258 A | 3/1987 | Drach | |
| 4,673,394 A | 6/1987 | Fenton, Jr. et al. | |
| 4,675,007 A | 6/1987 | Terry | |
| 4,691,943 A | 9/1987 | DeLand et al. | |
| 4,701,159 A | 10/1987 | Brown et al. | |
| 4,704,103 A | 11/1987 | Stöber et al. | |
| 4,723,948 A | 2/1988 | Clark et al. | |
| 4,769,017 A | 9/1988 | Fath et al. | |
| 4,772,276 A | 9/1988 | Wiita et al. | |
| 4,781,185 A | 11/1988 | Kauphusman et al. | |
| 4,786,089 A | 11/1988 | McConnell | |
| 4,823,805 A | 4/1989 | Wojcik | |
| 4,834,719 A | 5/1989 | Arenas | |
| 4,850,984 A | 7/1989 | Harris | |
| 4,880,414 A | 11/1989 | Whipple | |
| 4,890,866 A | 1/1990 | Arp | |
| 4,895,561 A | 1/1990 | Mahurkar | |
| 4,895,570 A | 1/1990 | Larkin | |
| 4,915,690 A | 4/1990 | Cone et al. | |
| 4,929,236 A | 5/1990 | Sampson | |
| 4,929,243 A | 5/1990 | Koch et al. | |
| 4,950,232 A | 8/1990 | Ruzicka et al. | |
| 4,950,255 A | 8/1990 | Brown et al. | |
| 4,963,133 A | 10/1990 | Whipple | |
| 4,983,161 A | 1/1991 | Dadson et al. | |
| 4,994,048 A | 2/1991 | Metzger | |
| 4,998,925 A | 3/1991 | Al-Sioufi et al. | |
| 5,000,614 A | 3/1991 | Walker et al. | |
| 5,040,831 A | 8/1991 | Lewis | |
| 5,053,015 A | 10/1991 | Gross | |
| 5,127,626 A | 7/1992 | Hilal et al. | |
| 5,129,891 A | 7/1992 | Young | |
| 5,167,647 A | 12/1992 | Wijkamp et al. | |
| 5,178,612 A | 1/1993 | Fenton, Jr. | |
| 5,209,740 A | 5/1993 | Bryant et al. | |
| 5,226,898 A | 7/1993 | Gross | |
| 5,257,622 A * | 11/1993 | Hooper et al. | 607/37 |
| 5,279,597 A | 1/1994 | Dassa et al. | |
| 5,282,790 A | 2/1994 | Clement | |
| 5,290,253 A | 3/1994 | Kira | |
| 5,312,337 A | 5/1994 | Flaherty et al. | |
| 5,314,411 A | 5/1994 | Bierman et al. | |
| 5,330,449 A | 7/1994 | Prichard et al. | |
| 5,354,282 A | 10/1994 | Bierman | |
| 5,360,407 A | 11/1994 | Leonard et al. | |
| 5,360,418 A | 11/1994 | Weilbacher et al. | |
| 5,380,301 A | 1/1995 | Prichard et al. | |
| 5,387,192 A | 2/1995 | Glantz et al. | |
| 5,399,168 A | 3/1995 | Wadsworth, Jr. et al. | |
| 5,405,339 A | 4/1995 | Kohnen et al. | |
| 5,417,672 A | 5/1995 | Nita et al. | |
| 5,423,775 A | 6/1995 | Cannon | |
| 5,456,671 A | 10/1995 | Bierman | |
| 5,456,676 A | 10/1995 | Nelson et al. | |
| 5,466,230 A | 11/1995 | Davila | |
| 5,551,849 A | 9/1996 | Christiansen | |
| 5,562,618 A | 10/1996 | Cai et al. | |
| 5,578,013 A | 11/1996 | Bierman | |
| 5,613,945 A | 3/1997 | Cai et al. | |
| 5,632,729 A | 5/1997 | Cai et al. | |
| 5,637,102 A * | 6/1997 | Tolkoff et al. | 604/536 |
| 5,697,951 A | 12/1997 | Harpstead et al. | |
| 5,702,371 A | 12/1997 | Bierman | |
| 5,743,873 A | 4/1998 | Cai et al. | |
| 5,792,104 A | 8/1998 | Speckman et al. | |
| 5,797,869 A | 8/1998 | Martin et al. | |
| 5,813,405 A | 9/1998 | Montano, Jr. et al. | |
| 5,827,230 A | 10/1998 | Bierman | |
| 5,830,401 A | 11/1998 | Prichard et al. | |
| 5,833,275 A | 11/1998 | Andersen | |
| 5,865,842 A | 2/1999 | Knuth et al. | |
| 5,913,852 A | 6/1999 | Magram | |
| 5,947,931 A | 9/1999 | Bierman | |
| 5,957,968 A | 9/1999 | Belden et al. | |
| 5,971,958 A | 10/1999 | Zhang | |
| 5,993,437 A | 11/1999 | Raoz | |
| 6,050,949 A | 4/2000 | White et al. | |
| 6,062,902 A | 5/2000 | Buckles et al. | |
| 6,065,075 A | 5/2000 | Ryzin et al. | |
| 6,068,622 A | 5/2000 | Sater et al. | |
| 6,074,379 A | 6/2000 | Prichard | |
| 6,113,572 A | 9/2000 | Gailey et al. | |
| 6,231,548 B1 | 5/2001 | Bassett | |
| 6,234,973 B1 | 5/2001 | Meador et al. | |
| 6,238,374 B1 | 5/2001 | Winkler | |
| 6,245,029 B1 | 6/2001 | Fujita et al. | |
| 6,254,589 B1 | 7/2001 | Raoz | |
| 6,273,404 B1 | 8/2001 | Holman et al. | |
| 6,290,676 B1 | 9/2001 | Bierman | |
| 6,332,874 B1 | 12/2001 | Eliasen et al. | |
| 6,350,260 B1 | 2/2002 | Goebel et al. | |
| 6,364,841 B1 | 4/2002 | White et al. | |
| 6,402,207 B1 | 6/2002 | Segal et al. | |
| 6,423,053 B1 * | 7/2002 | Lee | 604/533 |
| 6,428,515 B1 | 8/2002 | Bierman et al. | |
| 6,443,903 B1 | 9/2002 | White et al. | |
| 6,453,185 B1 | 9/2002 | O'Keefe | |
| 6,471,689 B1 | 10/2002 | Joseph et al. | |
| 6,506,182 B2 | 1/2003 | Estabrook et al. | |
| 6,517,115 B1 | 2/2003 | Blivet | |
| 6,517,520 B2 | 2/2003 | Chang et al. | |
| 6,554,802 B1 | 4/2003 | Pearson et al. | |
| 6,562,023 B1 | 5/2003 | Marrs et al. | |
| 6,572,555 B2 | 6/2003 | White et al. | |
| 6,579,261 B1 | 6/2003 | Kawamura | |
| 6,607,504 B2 | 8/2003 | Haarala et al. | |
| 6,612,624 B1 | 9/2003 | Segal et al. | |
| 6,641,177 B1 * | 11/2003 | Pinciaro | 285/242 |
| 6,652,489 B2 * | 11/2003 | Trocki et al. | 604/154 |
| 6,673,046 B2 | 1/2004 | Bierman et al. | |
| 6,676,652 B2 | 1/2004 | Mogg | |
| 6,679,528 B1 | 1/2004 | Poder | |
| 6,740,101 B2 | 5/2004 | Houser et al. | |
| 6,749,231 B2 | 6/2004 | LeMay et al. | |
| 6,749,574 B2 | 6/2004 | O'Keefe | |
| 6,796,586 B2 | 9/2004 | Werth | |
| 6,799,991 B2 | 10/2004 | Williams et al. | |
| 6,802,490 B2 | 10/2004 | Leinsing et al. | |
| 6,802,836 B2 | 10/2004 | Bouphavichith et al. | |
| 6,817,995 B1 | 11/2004 | Halpern | |
| 6,827,693 B2 | 12/2004 | White et al. | |
| 6,854,994 B2 | 2/2005 | Stein et al. | |
| 6,893,424 B2 | 5/2005 | Shchervinsky | |
| 6,997,900 B2 | 2/2006 | Westrate et al. | |
| 6,997,919 B2 | 2/2006 | Olsen et al. | |
| 7,014,627 B2 | 3/2006 | Bierman | |
| 7,044,936 B2 | 5/2006 | Harding et al. | |
| 2001/0049519 A1 | 12/2001 | Holman et al. | |
| 2002/0032436 A1 | 3/2002 | Mogg | |
| 2002/0062085 A1 | 5/2002 | White et al. | |
| 2002/0079696 A1 | 6/2002 | Szabo | |
| 2002/0082559 A1 | 6/2002 | Chang et al. | |
| 2002/0087059 A1 | 7/2002 | O'Keefe | |
| 2002/0151800 A1 | 10/2002 | White et al. | |
| 2002/0188255 A1 | 12/2002 | Bierman et al. | |
| 2003/0004520 A1 | 1/2003 | Haarala et al. | |
| 2003/0018293 A1 | 1/2003 | Tanghoj et al. | |
| 2003/0045912 A1 | 3/2003 | Williams et al. | |
| 2003/0077935 A1 | 4/2003 | Stein et al. | |

| | | | | | | |
|---|---|---|---|---|---|---|
| 2003/0097121 A1 | 5/2003 | Jolly et al. | | EP | 0 930 083 A3 | 10/1999 |
| 2003/0135148 A1 | 7/2003 | Dextradeur et al. | | EP | 1 138 343 A1 | 10/2001 |
| 2003/0158539 A1 | 8/2003 | Bouphavichith et al. | | EP | 1 181 946 A1 | 2/2002 |
| 2003/0181849 A1 | 9/2003 | Castellanos | | EP | 1 186 316 A2 | 3/2002 |
| 2003/0199853 A1 | 10/2003 | Olsen et al. | | EP | 0 691 868 B1 | 6/2002 |
| 2003/0209681 A1 | 11/2003 | Leinsing et al. | | EP | 1 033 146 B1 | 7/2002 |
| 2004/0039373 A1 | 2/2004 | Harding et al. | | EP | 1 219 319 A1 | 7/2002 |
| 2004/0044313 A1 | 3/2004 | Nakajima | | EP | 1 186 316 A3 | 5/2003 |
| 2004/0102736 A1 | 5/2004 | Bierman | | EP | 1 466 645 A2 | 10/2004 |
| 2004/0111056 A1 | 6/2004 | Weststrate et al. | | EP | 1 501 583 B1 | 5/2006 |
| 2004/0127854 A1* | 7/2004 | Leinsing et al. ....... 604/167.03 | | FR | 2 586 569 | 3/1987 |
| 2004/0158208 A1 | 8/2004 | Hiejima | | FR | 2 612 784 | 9/1988 |
| 2004/0181209 A1 | 9/2004 | Gross | | FR | 2 750 055 | 8/1998 |
| 2004/0181249 A1 | 9/2004 | Torrance et al. | | GB | 2 343 723 | 5/2000 |
| 2004/0204690 A1 | 10/2004 | Yashiro et al. | | GB | 2 343 723 A * | 5/2000 |
| 2004/0210249 A1 | 10/2004 | Fogarty et al. | | WO | WO 93/05844 A1 | 4/1993 |
| 2004/0236312 A1 | 11/2004 | Nistal et al. | | WO | WO 94/21315 A1 | 9/1994 |
| 2005/0033371 A1 | 2/2005 | Sommer et al. | | WO | WO 94/21319 A1 | 9/1994 |
| 2005/0107739 A1 | 5/2005 | Palma | | WO | WO 94/23775 A1 | 10/1994 |
| 2005/0137614 A1 | 6/2005 | Porter et al. | | WO | WO 95/19801 A1 | 7/1995 |
| 2005/0143714 A1* | 6/2005 | Hegland et al. ............. 604/533 | | WO | WO 95/19802 A1 | 7/1995 |
| 2005/0251102 A1* | 11/2005 | Hegland et al. ............ 604/500 | | WO | WO 97/25562 A1 | 7/1997 |
| 2005/0253389 A1 | 11/2005 | Schulte | | WO | WO 99/53981 A1 | 10/1999 |
| 2006/0127158 A1 | 6/2006 | Olson et al. | | WO | WO 00/13743 A1 | 3/2000 |
| | | | | WO | WO 00/24462 A1 | 5/2000 |
| | FOREIGN PATENT DOCUMENTS | | | WO | WO 01/91825 A2 | 12/2001 |
| DE | 24 56 166 | 8/1976 | | WO | WO 01/91847 A2 | 12/2001 |
| DE | 90 13 14 5 U1 * | 11/1990 | | WO | WO 01/091847 A3 | 7/2002 |
| DE | 90 13 145.2 | 1/1991 | | WO | WO 03/002171 A1 | 1/2003 |
| EP | 0 332 943 B1 | 9/1992 | | WO | WO 03/020368 A2 | 3/2003 |
| EP | 0 505 930 A2 | 9/1992 | | WO | WO 03/070151 A2 | 8/2003 |
| EP | 0 474 266 A2 | 11/1992 | | WO | WO 03/090840 A1 | 11/2003 |
| EP | 0 474 266 A3 | 11/1992 | | WO | WO 2004/016309 A2 | 2/2004 |
| EP | 0 505 930 A3 | 1/1993 | | WO | WO 2004/018015 A2 | 3/2004 |
| EP | 0 343 910 B1 | 6/1993 | | WO | WO 2001/091825 A3 | 4/2004 |
| EP | 0 559 662 B1 | 9/1993 | | WO | WO 2004/016309 A3 | 4/2004 |
| EP | 0 360 471 B1 | 4/1994 | | WO | WO 2004/016309 A3 | 6/2004 |
| EP | 0 415 665 B1 | 1/1995 | | WO | WO 2004/052272 A2 | 6/2004 |
| EP | 0 505 930 B1 | 6/1996 | | WO | WO 2004/060466 A1 | 7/2004 |
| EP | 0 229 729 B1 | 8/1996 | | WO | WO 2004/018015 A3 | 9/2004 |
| EP | 0 552 180 B1 | 12/1996 | | WO | WO 2004/052272 A3 | 10/2004 |
| EP | 0 504 325 B1 | 1/1997 | | WO | WO 2005/030316 A1 | 4/2005 |
| EP | 0 678 302 B1 | 2/1999 | | WO | WO 2006/036192 | 4/2006 |
| EP | 0 930 083 A2 | 7/1999 | | | | |

* cited by examiner

SQUEEZE-ACTUATED CATHETER CONNECTER AND METHOD

RELATED APPLICATION(S)

This application claims the benefit of U.S. Provisional Application No. 60/682,949, filed 20 May 2005, which is incorporated herein by reference in its entirety.

TECHNICAL FIELD

The present invention relates generally to implantable medical devices and, more particularly, to a connector for coupling medical tubing (e.g., a catheter) to an implantable device such as a drug infusion pump.

BACKGROUND

Treatment of diseases and ailments of the body often benefit from short- or long-term infusion of drugs and/or other fluids. While such medications may be administered extracorporeally, e.g., via transcutaneous injection, many patient benefit from the consistent and repeatable dosage provided by an implanted drug infusion pump. Such pumps may be used in a variety of applications such as control of pain and/or spasticity. They are well-suited to deliver infusate fluids to a targeted delivery site such as an epidural or intrathecal space of the spinal canal, or a particular location within the brain.

Drug infusion pumps are typically implanted subcutaneously, e.g., in the chest or abdominal cavity. The pump may incorporate a chamber to hold the infusate fluid. A needle-penetrable septum may also be provided and is preferably located generally directly beneath the skin. The septum allows drugs or other fluids to be introduced into the infusate chamber by transcutaneous injection. The pump may also include a fluid discharge outlet or stem through which the drug is directed during delivery. The outlet is typically connected to flexible medical tubing, e.g., a catheter, leading to the targeted delivery site.

A secure and leak-free connection of the catheter to the pump outlet is beneficial to ensure correct dosage delivery to the targeted delivery site. If the connection should somehow fail, the intended infusate dosage may not reach the delivery site and, moreover, some (or all) of the infusate could undesirably be dispensed in the vicinity of the pump outlet.

As may be appreciated by those skilled in the art, the connection of the delivery catheter to the discharge outlet may be subjected to various stresses attributable to movement of the patient, as well to other variables in patient physiology (e.g., weight changes, etc.). These factors may result in separating and/or twisting forces applied at the outlet/catheter connection that, over time, may degrade connection integrity.

Various concepts have sought to improve the strength of this connection. For example, raised circular barbs provided on the outlet may resist longitudinal sliding movement of the catheter away from the outlet. In other systems, a suture is provided in place of, or in addition to, the barbs. The sutures may cinch the catheter against the outlet, thereby providing additional resistance to relative catheter motion.

While effective, these catheter connections have drawbacks. For example, barbed stems may not be able to withstand the tensile forces exerted on the catheter due to movements of the patient, or may result in tearing of the catheter in the vicinity of the barb. Moreover, with regard to sutured connections, inherent variability in physician suturing techniques may result in a suture that is incorrectly placed relative to the catheter and connector. As a result, the suture may occlude or otherwise interrupt normal catheter flow. Even when the suture is correctly placed, it may be cinched too tightly—potentially cutting the catheter—or, alternatively, too loosely—potentially reducing the suture's ability to retain the catheter relative to the outlet.

SUMMARY

Embodiments of the present invention provide connectors and methods for connecting medical tubing (e.g., catheters) to an implantable infusion pump that may overcome these and other problems. In one embodiment, a connector for coupling a catheter to an implantable medical device is provided that includes a retaining member having a tubular sleeve with a cross-section defined by a major axis and an orthogonal minor axis. The retaining member further includes a locking finger that is positioned along the minor axis and extends inwardly from the sleeve. The retaining member is deflectable from a first position to a second position, wherein the locking finger, when in the second position, is displaced outwardly from its location in the first position.

In another embodiment, a method for connecting a catheter to a medical device is provided. The method includes inserting a stem of the medical device into a connector. The connector includes: a housing having a tubular wall defining a window extending radially through the tubular wall; and a retaining member to surround at least a portion of the housing. The retaining member includes: a tubular sleeve having a cross-sectional shape defined by both a major axis and an orthogonal minor axis; and a locking finger positioned along the minor axis such that it protrudes inwardly from the tubular sleeve. The method further includes passing the locking finger through the window of the tubular wall; and engaging the locking finger with the stem of the medical device.

In still yet another embodiment, an implantable medical system is provided including an implantable medical device, a catheter comprising a proximal end, and a connector for coupling the proximal end of the catheter to the implantable medical device. The connector includes a housing having a tubular wall defining a window that extends radially through the tubular wall. The housing is configured to surround the proximal end of the catheter and a stem of the implantable medical device. The connector may also include a retaining member to surround at least a portion of the housing. The retaining member includes: a tubular sleeve having a cross-section defined by a major axis and an orthogonal minor axis; and a locking finger positioned along the minor axis of the sleeve and extending inwardly therefrom. The retaining member is deflectable from a first position, wherein the locking finger extends inwardly through the window of the housing, to a second position, wherein the locking finger is located outwardly from the first position.

The above summary is not intended to describe each embodiment or every implementation of the present invention. Rather, a more complete understanding of the invention will become apparent and appreciated by reference to the following Detailed Description of Exemplary Embodiments in view of the accompanying figures of the drawing.

BRIEF DESCRIPTION OF THE VIEWS OF THE DRAWING

The present invention will be further described with reference to the figures of the drawing, wherein:

FIGS. 1A and 1B illustrate implanted infusion pump systems incorporating a catheter connector in accordance with embodiments of the present invention; wherein FIG. 1A illustrates a brain infusion system; and FIG. 1B illustrates a spinal infusion system;

Unless stated otherwise herein, the figures of the drawing are rendered primarily for clarity and thus may not be drawn to scale.

DETAILED DESCRIPTION OF EXEMPLARY EMBODIMENTS

In the following detailed description of illustrative embodiments of the invention, reference is made to the accompanying figures of the drawing that form a part hereof, and in which are shown, by way of illustration, specific embodiments in which the invention may be practiced. It is to be understood that other embodiments may be utilized and structural changes may be made without departing from the scope of the present invention.

In general, embodiments of the present invention are directed to connector apparatus, systems, and methods for connecting medical tubing, e.g., catheters, to a source device such as an implantable medical device. Preferably, the connectors and methods described herein provide substantially leak-free and secure coupling of the catheter to the device at implantation, yet may readily permit disconnection and removal by a physician when desired.

It is noted that the terms "comprises" and variations thereof do not have a limiting meaning where these terms appear in the accompanying description and claims. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used herein only to simplify the description, however, and not to limit the scope of the invention in any way.

Figure 1A:
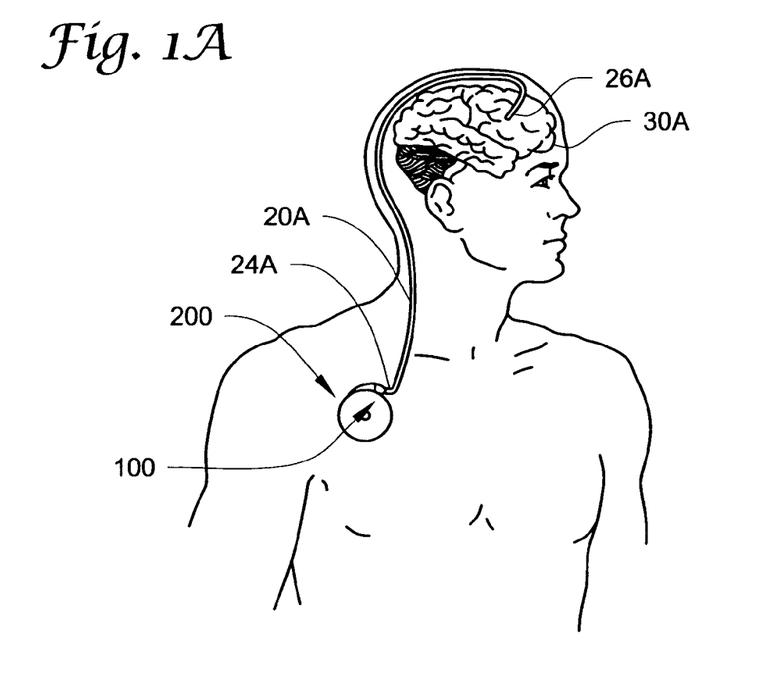
Figure 1B:
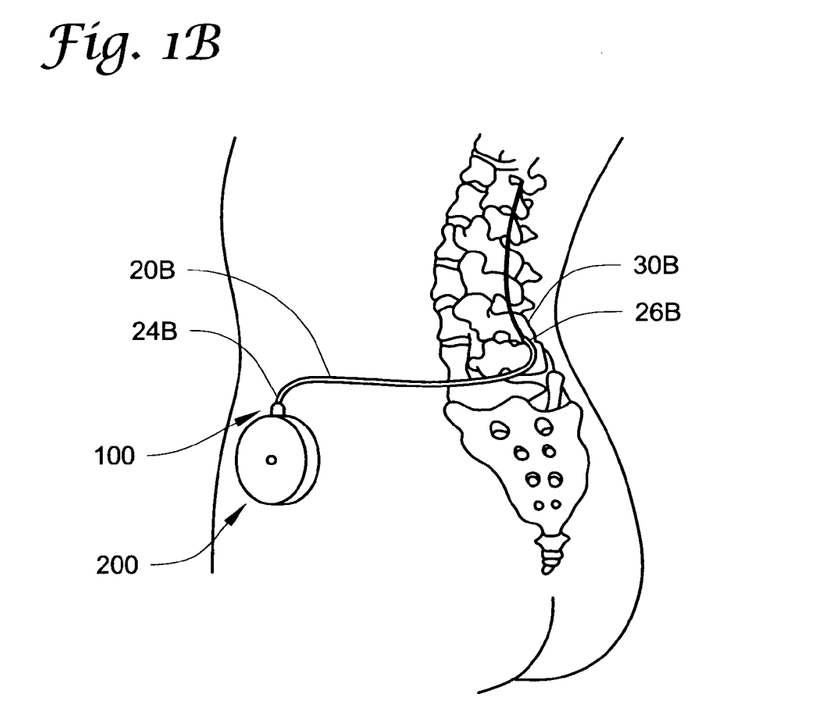

FIGS. 1A and 1B illustrate exemplary implantable medical systems that may utilize a connector and method in accordance with embodiments of the present invention. FIG. 1A illustrates an implantable drug infusion pump 200 (e.g., an ISOMED or SYNCHROMED infusion pump sold by Medtronic, Inc. of Fridley, Minn., USA) configured to deliver an infusate drug to a specific location within the brain 30A. A catheter, e.g., catheter 20A, may include a proximal end 24A coupled to the pump 200, and a distal end 26A positioned near the targeted delivery site in the brain 30A. A connector 100 in accordance with one embodiment of the present invention may be used to couple the catheter 20A to the pump 200. While a pump 200 is provided in the embodiment shown, the pump could be replaced with a variety of other implantable medical devices.

FIG. 1B illustrates another exemplary infusion system wherein a distal end 26B of a catheter, e.g., catheter 20B, is positioned within a spinal column 30B. The proximal end 24B is, once again, coupled to the pump 200 with a connector in accordance with an embodiment of the present invention, e.g., the connector 100.

While the exact size and construction of each catheter 20A and 20B (generically referred to herein as "catheter 20") may vary without departing from the scope of the invention, each may, in one embodiment, be formed from extruded silicone tubing. In the illustrated applications, the catheter 20 may have an undeflected outer diameter of, e.g., about 1 to about 3 millimeters (mm). Other exemplary medical tubing materials may include polyurethane and co-extrusions such as silicone/polyurethane.

Figure 2:
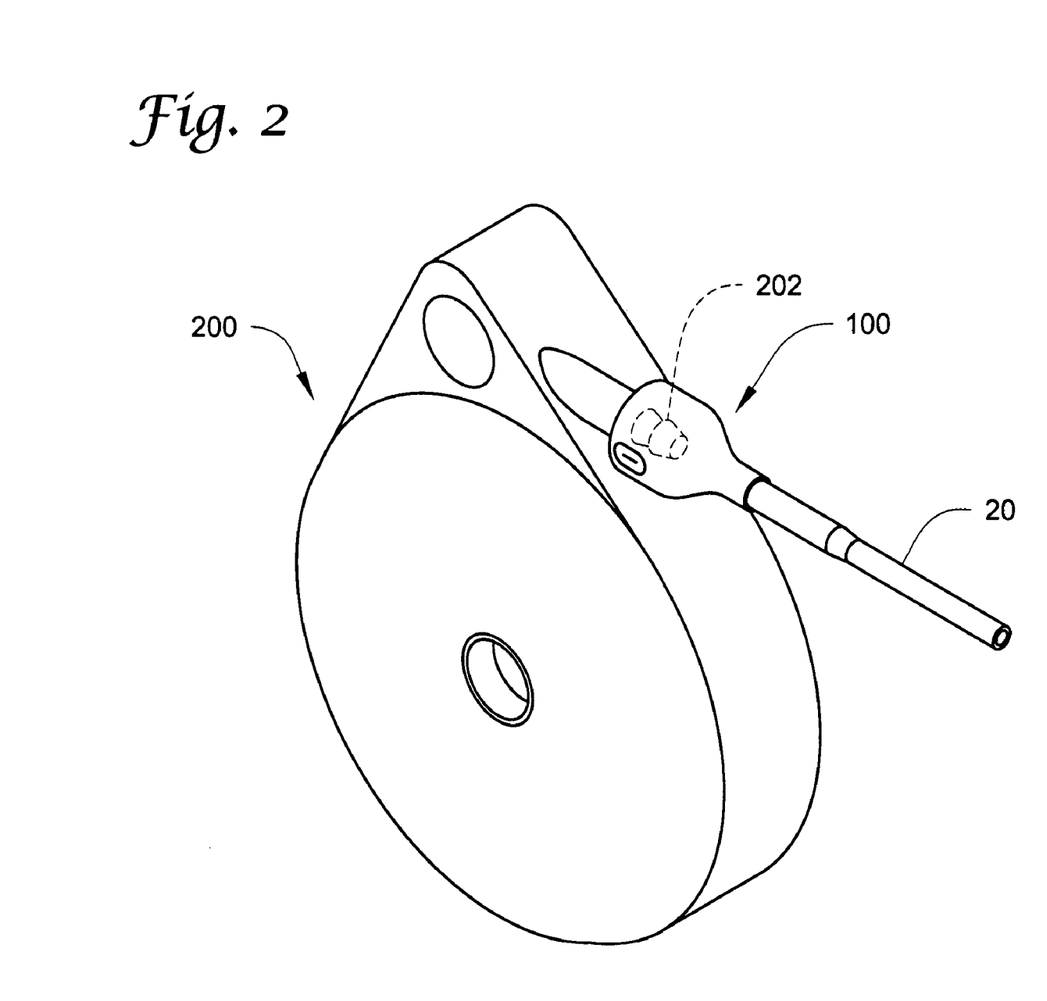
FIG. 2 is an enlarged view of the infusion pump and catheter connector of FIGS. 1A and 1B.

FIG. 2 illustrates an enlarged perspective view of the pump 200 and connector 100 of FIGS. 1A and 1B. Although not fully illustrated in FIG. 2, the pump 200 may include a discharge port or stem 202 (see FIG. 3) to which the catheter 20 attaches and through which infusate from the pump is delivered. The stem 202 may form a tapered cylinder having raised barbs 204 thereon (see FIG. 3), yielding a "Christmas tree" shape to better engage an inner surface of the catheter as described below and illustrated in FIG. 7.

Figure 3:
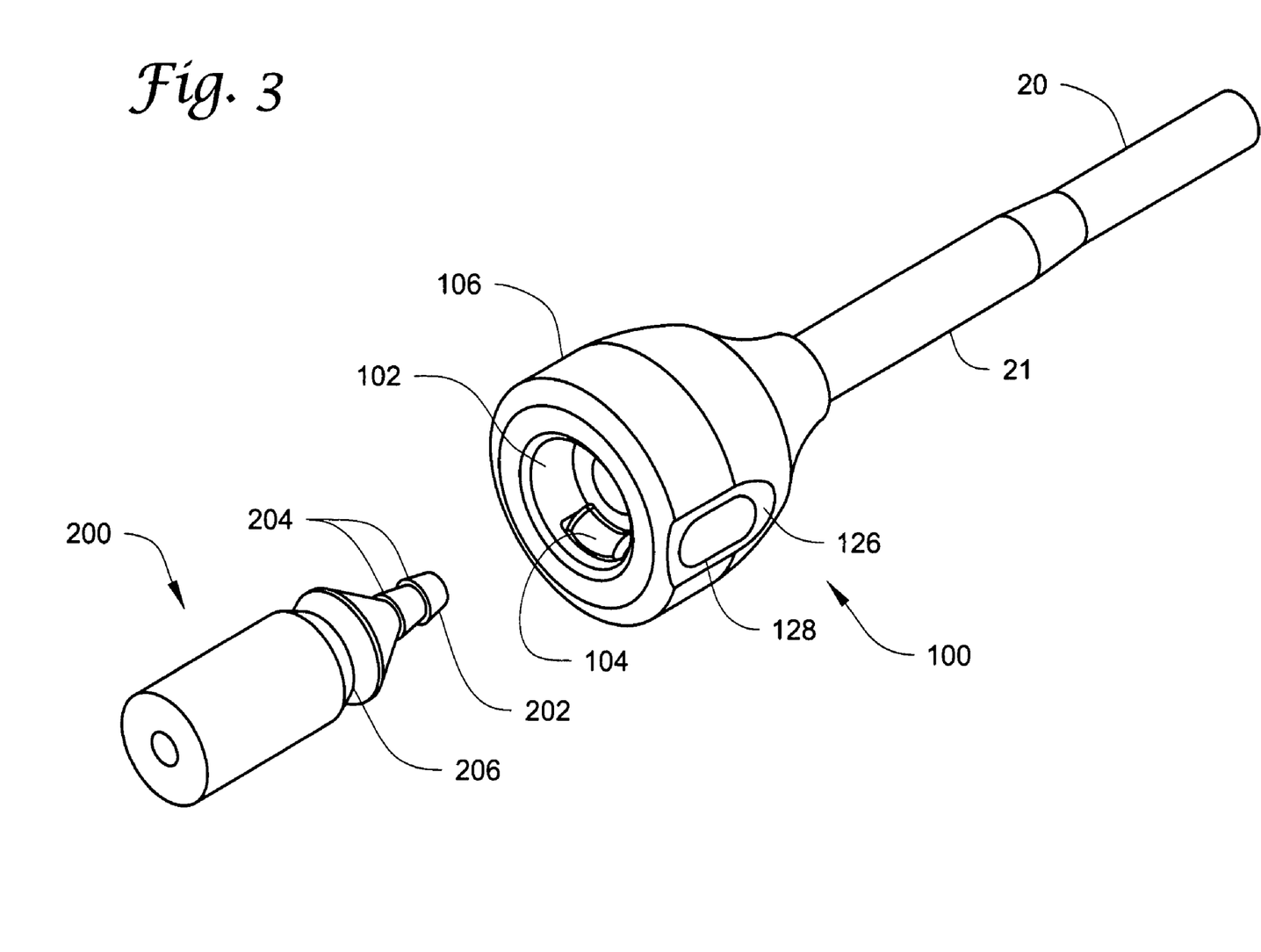
FIG. 3 is an enlarged view of the catheter connector of FIG. 2 detached from the pump.

As FIG. 3 illustrates, the proximal end of the catheter 20 (the end that attaches to the pump 200) may include a seal 21 attached thereto, e.g., via mechanical capture, adhesive, press fit, or the like. Alternatively, the seal 21 could be over-molded with the catheter (e.g., silicone over silicone catheter) or otherwise formed as an integral portion thereof. FIG. 3 illustrates other various components that are described in more detail below.

Suitable materials for the seal 21 may include molded silicone or polyurethane. Preferably, the seal is relatively flexible (as compared to the housing 102 described further below). However, use of other materials for the seal, including those that are more rigid, is certainly possible without departing from the scope of the invention.

Figure 4:
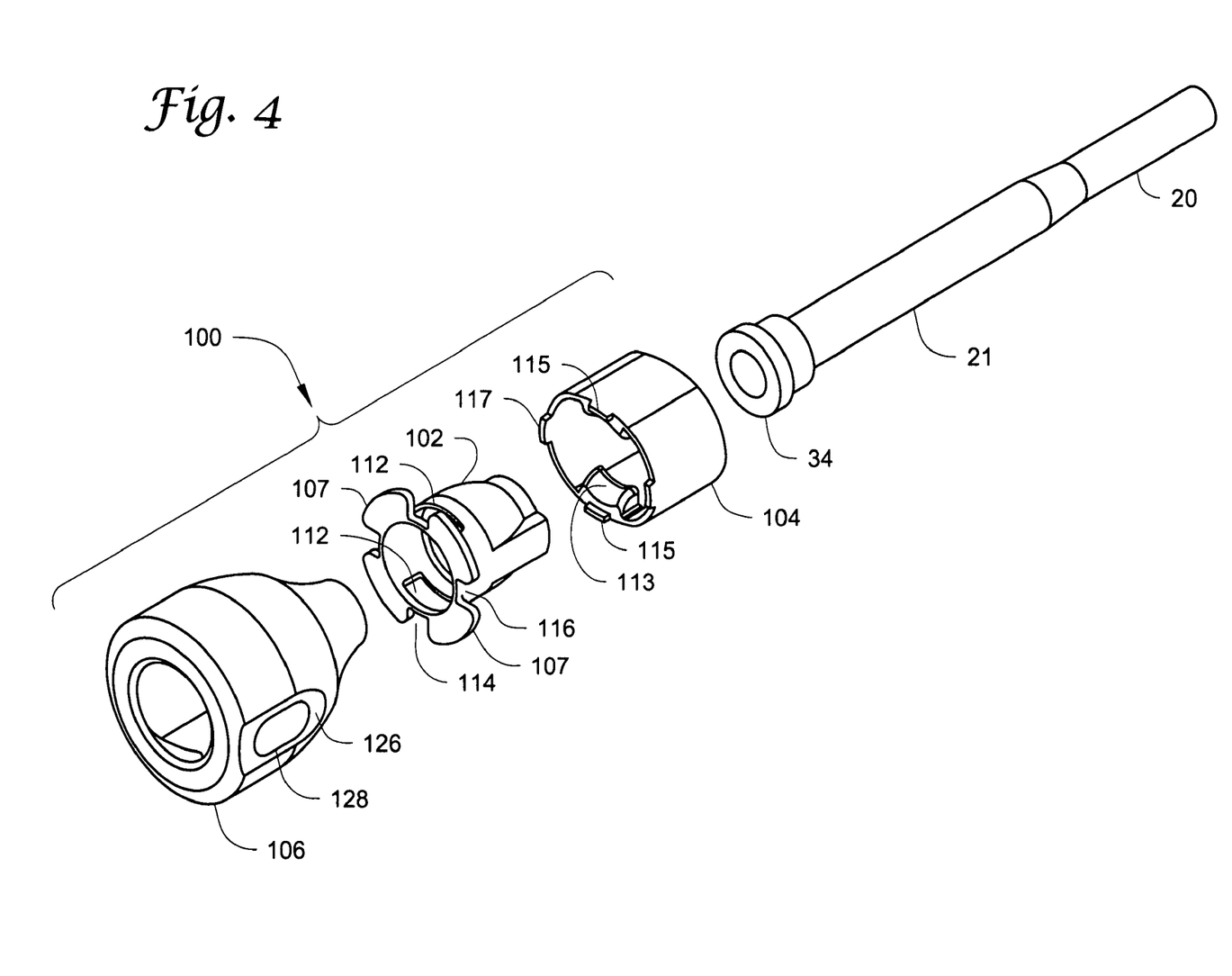
FIG. 4 is an exploded view of the connector of FIG. 3.

FIG. 4 is an exploded view of the exemplary catheter connector 100. As clearly illustrated in this view, the connector 100 may include a retaining member 104 and an optional housing 102. When the stem 202 is adequately coupled to the catheter 20 and connector 100 as further described below, one or more locking surfaces or fingers 113 of the retaining member 104 may engage a receiving portion of the stem (e.g., a groove 206 formed in the stem 202 as shown in FIG. 3), thereby securely coupling the catheter to the pump 200. FIG. 4 also illustrates and identifies other components that are described in more detail below.

An optional cover member, e.g., boot 106, may slide axially to cover the housing 102 and retaining member 104 as indicated in FIG. 3. The boot 106 may be configured to reduce stress on surrounding tissue by providing a relatively smooth transition surface around the connector 100. The boot 106 may also reduce or prevent excessive tissue growth within the internal parts of the connector 100. The boot 106 may, in one embodiment, be made of silicone rubber, e.g., white ETR silicone, and may optionally be loaded (e.g., 12.5% Barium Sulfate loaded or 2% Titanium Dioxide loaded) to give the connector a degree of radiopaqueness. While other materials are certainly possible, the use of silicone rubber provides the connector with a soft, impact-absorbent exterior.

While the connector 100 is illustrated herein as operable to couple the stem 202 of the implantable medical device 200 to a female end of the catheter 20, such a configuration is not limiting. For example, the connector 100 could also be utilized with reversed configurations, e.g., an implantable drug infusion pump having a female-configured end (e.g., similar to the illustrated end of the catheter 20), while the catheter could include a male-configured stem (e.g., similar to the illustrated stem 202).

Figure 5:
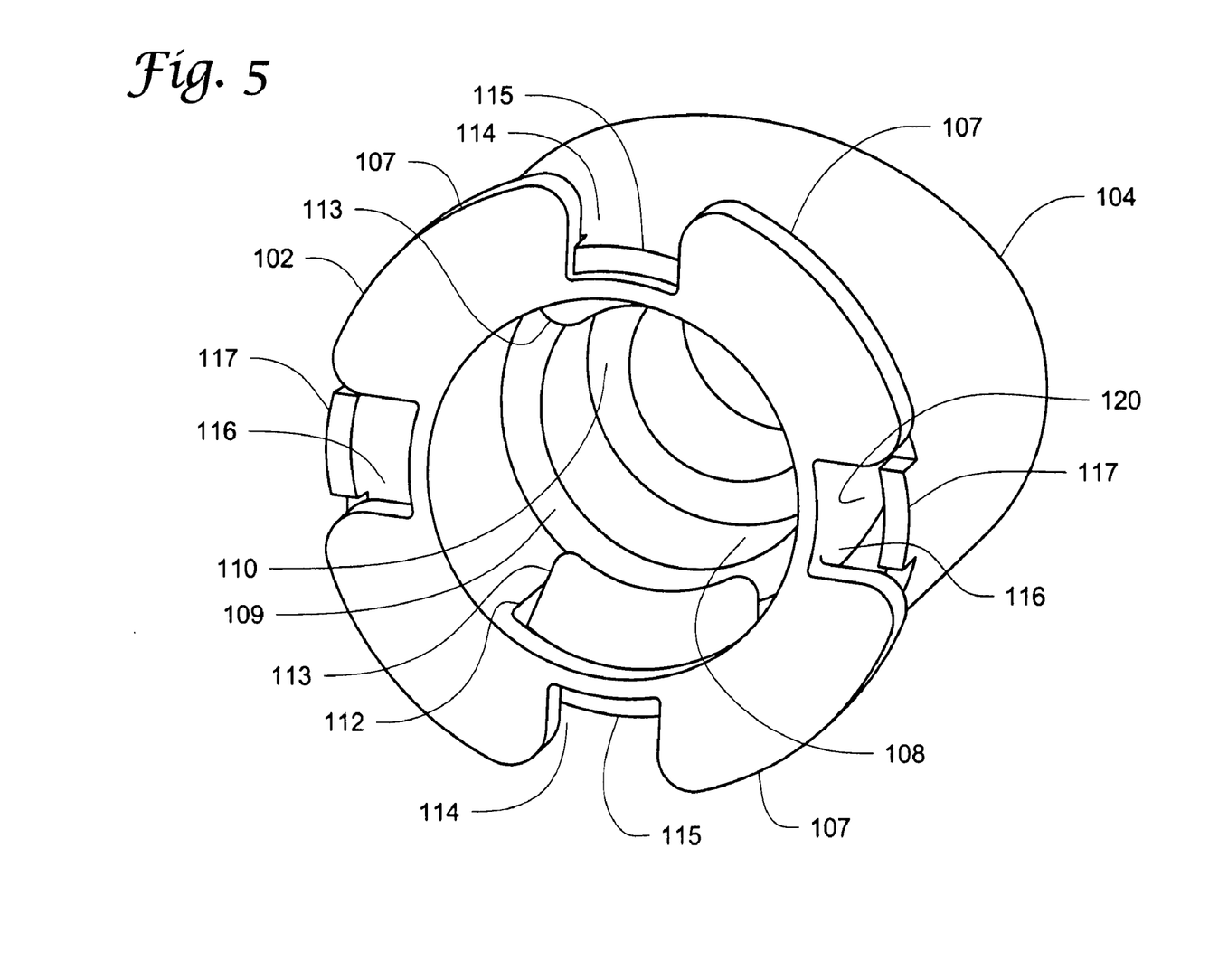
FIG. 5 is an enlarged view of an exemplary retaining member and housing of the connector of FIGS. 2 and 3.

FIG. 5 is an enlarged perspective view of a portion or subassembly of the connector 100 of FIG. 4. This subassembly may include the housing 102 and the retaining member 104. As clearly illustrated in this view, the housing and retaining member define generally tubular or sleeve-shaped members.

The housing 102 may include a tubular wall of a generally circular cross-section, and may include a housing flange 107 at one end ("cross-section," as used herein, indicates a section view taken along an identified line of sight or, where no line of sight is identified, along a conventional, e.g., longitudinal, axis of the referenced component). In the illustrated embodiment, a stepped lumen 108 extends through the housing, wherein the steps define one or more abutting surfaces. For example, the steps may define a first abutting surface 109 and a second abutting surface 110. The abutting surfaces 109, 110 may contact corresponding surfaces of the seal 21, as described in more detail below, to assist in maintaining the integrity of the connection.

The housing 102 may further include one or more slots. In the illustrated embodiments, these slots are formed in the housing flange 107 as shown in FIG. 5. For instance, the housing 102 may include first or vertical slots 114 positioned along a minor axis 103 (see FIG. 6) of the retaining member 104, and second or horizontal slots 116 positioned along the retaining member's major axis 105. The slots 114 and 116 may receive tabs, e.g., vertical tabs 115 and horizontal tabs 117, respectively, of the retaining member 104. The tubular housing 102 may further include one or more windows 112 (only one visible in FIG. 5) through which the one or more locking fingers 113 associated with the retaining member may selectively protrude as further described below. In the illustrated embodiment, there are two windows on opposing sides of the housing 102, and two locking fingers 113 on opposing sides of the retaining member 104.

In the illustrated embodiments, the housing 102 is preferably made of a relatively rigid, biocompatible material such as titanium, stainless steel, or rigid plastic. The housing may be produced by most any acceptable manufacturing process, e.g., machining, injection molding, etc.

Figure 6:
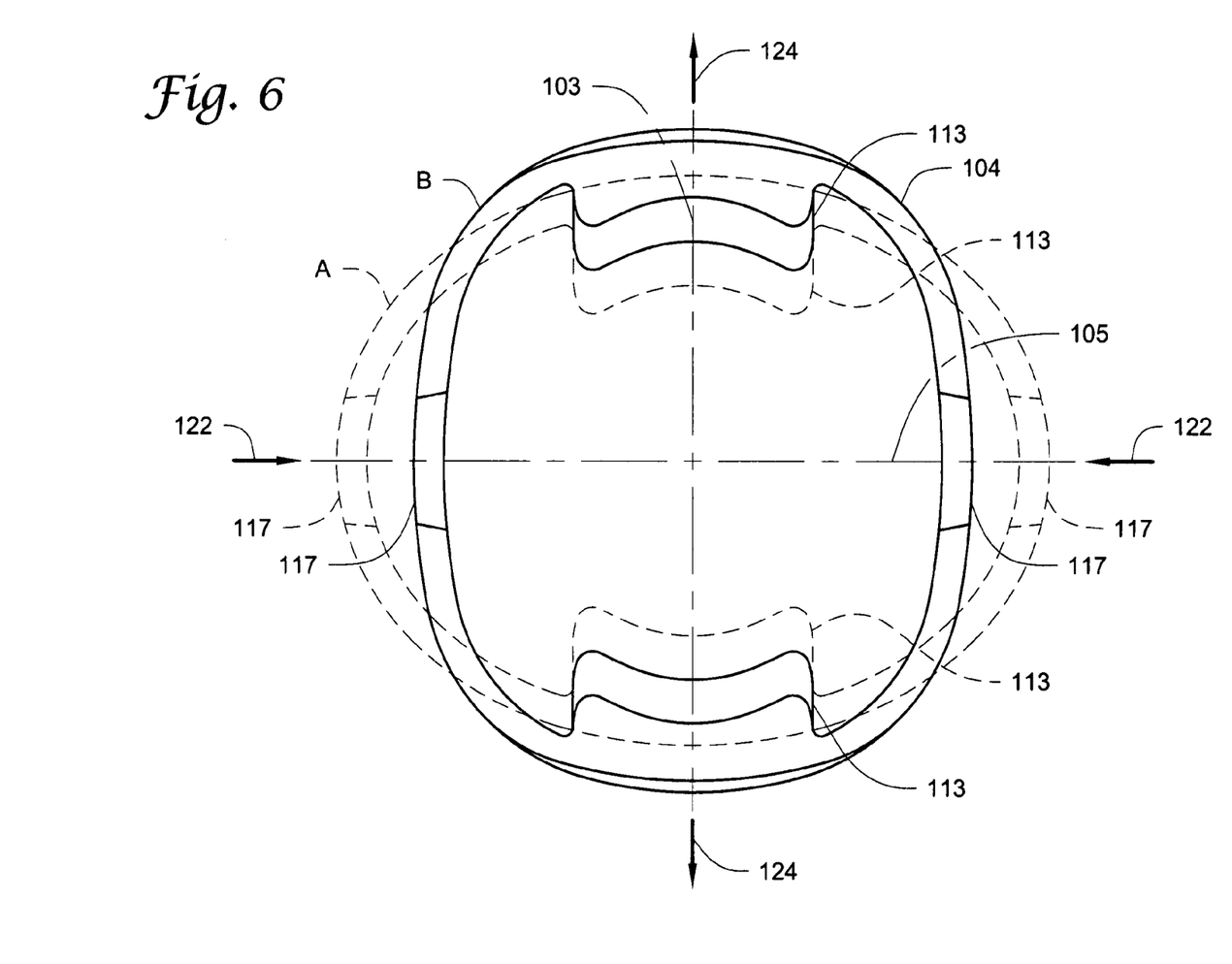
FIG. 6 is a diagrammatic end view of the retaining member of FIG. 5, wherein the retaining member is shown in a first or unactuated position A, and a second or actuated position B.

FIG. 6 illustrates an end view of the retaining member 104, which, as shown in FIGS. 3-5, surrounds the housing 102 during use. In the illustrated embodiment, the retaining member is deflectable and is shaped such that, when undeflected and viewed along its longitudinal axis (or in cross-section) as shown in FIG. 6, it defines a minor axis 103 and a major axis 105. The major axis 105 may span across the widest cross-sectional opening of the retaining member 104, while the minor axis 103, which is preferably orthogonal to the major axis 105, may span across a narrower portion, e.g., the smallest cross-sectional opening. While a variety of shapes may yield this configuration, the retaining member 104 is, in one embodiment, configured as a tubular sleeve with a generally elliptical cross-section (e.g., when viewed along its longitudinal axis) as shown in FIGS. 4-6. As a result, the greatest dimension or diameter of the ellipse (e.g., a line extending through the foci) defines the major axis 105.

As described above, the retaining member 104 may further include one or more locking fingers 113 protruding or extending inwardly from the tubular sleeve. The locking fingers 113 are preferably positioned along the minor axis 103 such that they pass through the corresponding windows 112 of the housing 102 (see FIG. 5) and selectively engage a receiving portion of the stem 202 (e.g., a groove 206 formed in the stem) of the pump 200 as further described below.

The retaining member 104 may further include the vertical and horizontal tabs 115 and 117 that correspond in location to the vertical and horizontal slots 114 and 116 of the housing, respectively. That is, the vertical tabs 115 may be positioned along the minor axis 103, while the horizontal tabs 117 may be positioned along the major axis 105 (for clarity, the vertical tabs 115 are not illustrated in FIG. 6).

The increased width of the retaining member 104 along its major axis 105 results in a clearance between the retaining member 104 and the generally cylindrically shaped (e.g., circular cross-section) housing 102 along the major axis. For example, when the retaining member is in a first or unactuated (e.g., relaxed) position A as shown in FIG. 5, little or no clearance exists between the minor axis 103 of the retaining member 104 and the housing, i.e., in the vicinity of the vertical tabs 115. However, when in this unactuated position, a gap 120 preferably exists along the major axis 105 between the retaining member 104 and the housing, i.e., in the vicinity of the horizontal tabs 117. The gap 120 is beneficial as it provides space for compression of the retaining member 104. That is, the gap 120 allows the retaining member to elastically deflect from the first unactuated position A to a second actuated position B (see FIG. 6) without interference with the housing 102. Such actuation permits disengagement of the connector 100 (and thus the catheter) from the pump 200.

To actuate the retaining member 104, a horizontal compressive force 122 may be applied near the horizontal tabs 117, e.g., along the major axis 105 of the retaining member 104. The horizontal compressive force 122 may be applied by "squeezing" the retaining member, for example, between a physician's thumb and forefinger. As the retaining member 104 is compressed, the locking fingers 113 move outwardly (relative to the first position) along the minor axis 103 (e.g., move in the direction indicated by arrows 124 in FIG. 6). As a result, the locking fingers 113 move from the first unactuated position A outwardly through the windows 112 (see FIG. 5).

The fingers 113 need only withdraw sufficiently to disengage from the stem. That is, when the retaining member is in the first unactuated position A, the locking fingers protrude inwardly through the window a first distance, while, when in the second actuated position B, the locking fingers may either: withdraw from the window; or protrude inwardly through the window a second distance that is less than the first distance.

In the illustrated embodiment, the gap 120 (see FIG. 5) permits elastic deflection of the retaining member 104 horizontally inwardly about 1 mm on each side. This movement results in vertical outward displacement of each locking finger 113 (away from the housing) of about 0.5 to about 0.7 mm, e.g., about 0.64 mm. The relatively rigid housing 102 may act as a stop, preventing the physician from over-squeezing and permanently deforming or breaking the retaining member 104.

The retaining member 104 is preferably made from a relatively flexible material to permit snap-fit engagement between the locking fingers 113 and the windows 112 of the housing. Exemplary materials may include injection-molded nylon (e.g., Grilamid TR55 Nylon 12 produced by EMS-Grivory), polysulfone (e.g., Udel Polysulfone P-1700 produced by Solvay Advanced Polymers, L.L.C.), or other engineering plastics.

The interrelation of the vertical and horizontal tabs 115, 117 of the retaining member 104 with the vertical and horizontal slots 114, 116 of the housing 102 assist in properly aligning the vertical and horizontal axes of the two components, relative to one another, during actuation. For example, the engagement of the vertical tabs 115 with the vertical slots 114 assists in maintaining the locking fingers 113 in alignment with the windows 112. Similarly, the engagement of the horizontal tabs 117 with the horizontal slots 116 assists in maintaining substantially equivalent displacement of each locking finger 113. Without the tabs 117 and slots 116, one locking finger 113 could remain stationary while the remaining finger could move twice its intended displacement. While the horizontal and vertical tabs provide these desirable alignment benefits, other embodiments may eliminate some or all of these tabs without departing from the scope of the invention. Still further, while the housing 102 is beneficial for reasons described herein, other embodiments may eliminate the housing altogether without departing from the scope of the invention.

Figure 7:
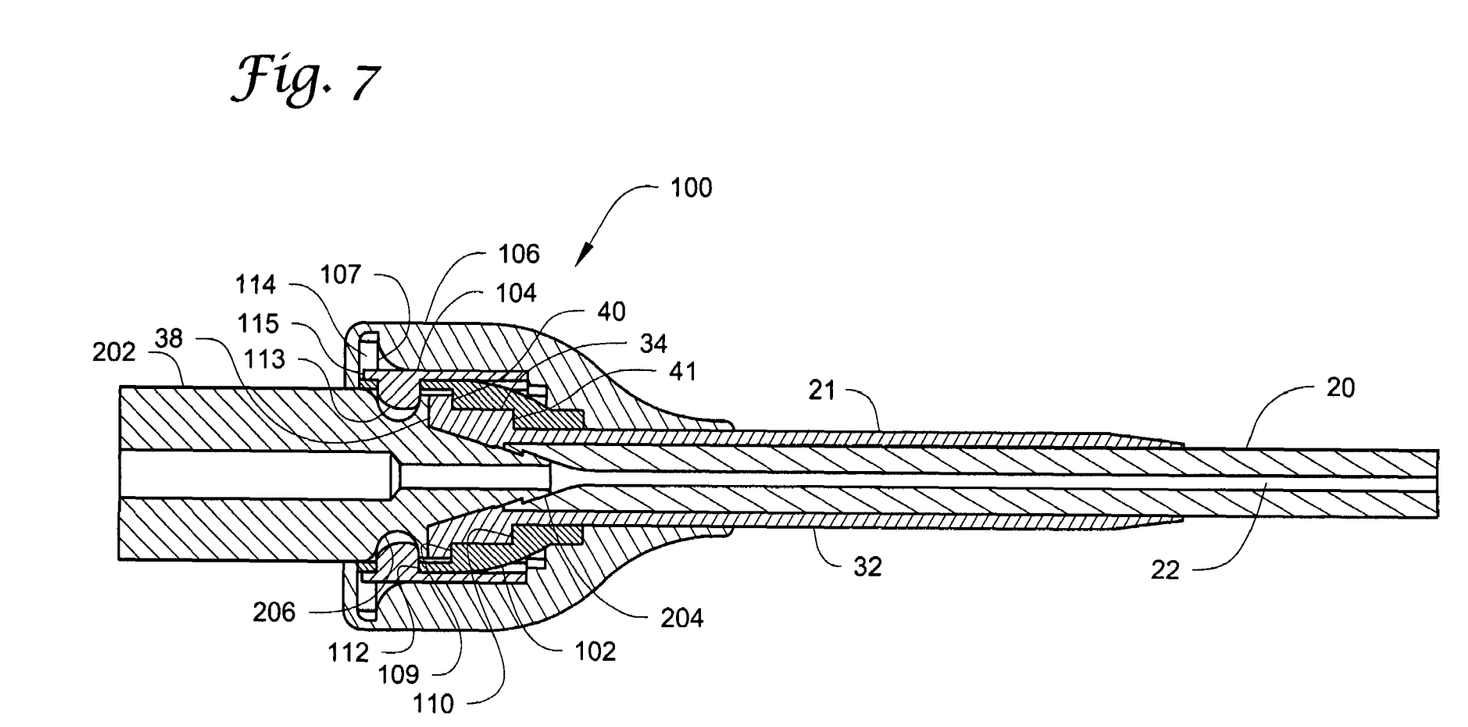
FIG. 7 is a section view of the connector of FIG. 2 as attached to a stem of the infusion pump.

FIG. 7 illustrates a cross-sectional view of the exemplary connector 100 as it is used to couple the catheter 20 to the stem 202 of the infusion pump 200. As described above, the catheter 20 may include the seal 21, wherein the seal may include both an elongate body portion 32, and a flange portion 34 defined by a generally cylindrical but stepped surface. In the illustrated embodiment, the catheter 20 may extend through the body portion 32 and into the flange portion 34 of the seal 21. A lumen, which may be tapered, extends from a face 38 of the seal 21 to a lumen 22 of the catheter 20. As a result, when the seal 21 is coupled to the stem 202, the lumen 22 of the catheter 20 is in fluid communication with an infusate chamber of the pump 200.

The flange portion 34 of the seal 21 may form one or more axial compression surfaces, e.g., first compression surface 40 and second compression surface 41, that are normal to an axis of the catheter. The surfaces 40 and 41 may contact the abutting surfaces 109 and 110, respectively, of the housing 102, as illustrated by FIG. 7, when the connector 100 is positioned to couple the pump 200 to the catheter 20. While illustrated as incorporating the seal 21 and flange portion 34, other catheter embodiments lacking these features are also contemplated. For example, a catheter having a tapered end could be substituted without departing from the scope of the invention.

During use, the retaining member 104 and housing 102 may be preassembled as shown in FIG. 5 and slid over a distal end of the catheter 20 and seal 21 until the abutting surfaces 109 and 110 contact the compression surfaces 40 and 41 of the seal (or the distal end could be overmolded after the seal 21 is inserted into the housing 102). The optional boot 106 may then be slid over the distal end of the catheter 20 and positioned a short distance from the housing 102 and the retaining member 104.

The stem 202 may then be inserted into the connector, e.g., into the lumen of the flange portion 34 of the seal 21, such that at least a portion of both the stem and catheter 20 are surrounded by the housing 102. The stem 202 may be inserted until the tip of the stem penetrates the end of the catheter by a small amount (e.g., about 1.4 mm; which, in one embodiment, may be about 0.64 mm past the outer edge of the first barb 204). Upon insertion, the locking fingers 113 of the retaining member 104, which extend through the windows 112 of the housing 102, may deflect towards their second positions as they pass over the lip that defines the groove 206. Once the locking fingers reach the groove 206 of the stem 202, they may return to their first (undeflected) positions whereby they engage, e.g., snap into, the groove. In the illustrated embodiment, there is about 0.5 mm (per side) engagement of the fingers 113 with the groove 206 of the stem. When the fingers 113 are locked with the groove 206, the seal 21 may form a compression axial seal against a front face of the stem 202. In one embodiment, there is about 0.3 mm interference (compression) of the seal against the stem when the catheter is coupled thereto.

The boot 106 may then be slid toward the proximal end of the catheter 20 until it covers the retaining member 104 as shown in FIG. 7. Alternatively, the boot 106 could be positioned over, e.g., assembled with, the housing 102 prior to coupling the catheter 20 to the stem 202, in which case the boot 106 would be positioned with the housing 102 during interconnection with the pump 200.

To remove the catheter 20 from the pump 200, the connector 100 may be actuated to disengage the locking fingers 113 from the stem 202 as described above. The boot 106 may include one or more features that assist the physician with actuation of the connector. For example, as shown in FIGS. 3 and 4, the boot may include diametrically opposing flat surfaces 126 (only one shown) on its exterior. These flat surfaces may align with the horizontal tabs 117 of the retaining member, e.g., align with the major axis 105, thereby providing the physician with a tactile indication of where compressive force 122 (see FIG. 6) should be applied. In place of the flat surfaces 126, or in addition thereto, the boot 106 may also include visual markings 128, as shown in FIGS. 3 and 4, to indicate the correct location for the application of the compressive force. The compressive force 122 necessary to actuate the connector may vary. However, in one embodiment, it is preferably about 1 to about 10 pounds-force (lbf) (about 4 to about 44 Newtons (N)), and, more preferably, about 5 to about 10 lbf (about 22 to about 44 N).

Much of the stress of external bending moments that are experienced by the connector 100 may be carried by the housing 102, which surrounds the stem 202 on both sides of the groove 206, providing a large region over which load can be distributed. Accordingly, the primary loading on the locking fingers 113 is desirably an axial, shear load for which the fingers are adapted to react. The connector 100 thus provides secure coupling capable of withstanding stress levels typically encountered during implantation.

While the connector assemblies illustrated herein may be scaled for use with most any size of catheter, an exemplary infusion pump/catheter connector as described herein may utilize a housing 102 having an outer body diameter of about 5 to about 7 mm (e.g., about 5.8 mm) and a length of about 6 to about 8 mm (e.g., about 7.3 mm) for a catheter having a diameter of about 2 mm. The boot 106 may have an outer diameter of about 8 to about 10 mm (e.g., about 9.1 mm) and a length of about 10 to about 15 mm (e.g., about 12.5 mm). The overall volume of the connector 100 may be less than about 1 cubic centimeter (cc), preferably less than about 0.95 cc, and more preferably, less than about 0.65 cc.

Embodiments of the present invention provide a relatively low-profile catheter/pump connector that may be intuitively locked and unlocked without resort to the use of tools. Moreover, the components of the connector are captivated, reducing the risk of lost or misplaced parts. Still further, the snap-fit nature of the connector provides the physician with tactile and/or auditory feedback when the locking fingers engage the stem groove. Still further, connectors in accordance with embodiments of the present invention provide excellent resistance to catheter separation when subjected to anatomically-induced separating forces, yet may be unlocked (via physician actuation) to permit removal with minimal pulling force.

Illustrative embodiments of this invention are discussed and reference has been made to possible variations within the scope of the invention. These and other variations, combinations, and modifications in the invention will be apparent to those skilled in the art without departing from the scope of the invention, and it should be understood that this invention is not limited to the illustrative embodiments set forth herein. Accordingly, the invention is to be limited only by the claims provided below, and equivalents thereof.

What is claimed is:

1. A connector for coupling a catheter to an implantable medical device, the connector comprising:
    a retaining member comprising:
        a tubular sleeve having a cross-section defined by a major axis and an orthogonal minor axis; and
        a locking finger positioned along the minor axis and extending inwardly from the sleeve;
        wherein the retaining member is deflectable from a first position to a second position such that the locking finger, when the retaining member is in the second position, is displaced outwardly from a location of the locking finger when the retaining member is in the first position; and
    a housing surrounded by the retaining member, the housing comprising:
        a tubular wall defining a radial window operable to receive the locking finger, wherein the housing is configured to operatively surround both an end of the catheter and a stem of the implantable medical device; and
        a housing flange that defines a first slot positioned along the minor axis of the retaining member, and a second slot positioned along the major axis of the retaining member, wherein the retaining member comprises a tab positioned to fit within the first slot and the second slot.

2. The connector of claim 1, wherein the window is alignable with the stem of the medical device such that, when the retaining member is in the first position, the locking finger is engageable with a receiving portion of the stem.

3. The connector of claim 1, wherein the tubular wall of the housing defines two windows on opposing sides of the housing, and wherein the retaining member comprises two locking fingers positioned along the minor axis on opposing sides of the retaining member.

4. The connector of claim 1, further comprising a cover member that at least partially encloses the retaining member.

5. The connector of claim 1, wherein the housing comprises a transverse, circular cross-section and the retaining member comprises a transverse, elliptical cross-section.

* * * * *